(12) United States Patent
Gross

(10) Patent No.: US 11,621,056 B2
(45) Date of Patent: Apr. 4, 2023

(54) COMPRESSION AND ANNOTATION OF DIGITAL WAVEFORMS FROM SERIAL READ NEXT GENERATION SEQUENCING TO SUPPORT REMOTE COMPUTING BASE CALLING

(71) Applicant: KONINKLIJKE PHILIPS N.V., Eindhoven (NL)

(72) Inventor: Brian David Gross, North Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1348 days.

(21) Appl. No.: 15/960,872

(22) Filed: Apr. 24, 2018

(65) Prior Publication Data

US 2018/0314791 A1 Nov. 1, 2018

Related U.S. Application Data

(60) Provisional application No. 62/490,720, filed on Apr. 27, 2017.

(51) Int. Cl.
*G16B 30/00* (2019.01)
*G16B 20/00* (2019.01)
(Continued)

(52) U.S. Cl.
CPC .............. *G16B 30/00* (2019.02); *G16B 20/00* (2019.02); *G16B 50/10* (2019.02); *G16B 50/50* (2019.02);
(Continued)

(58) Field of Classification Search
CPC ........ G16B 30/00; G16B 50/50; G16B 20/00; G16B 50/10; C12Q 1/6869; H04L 5/22; H04L 47/34; H04L 67/12
See application file for complete search history.

(56) References Cited

U.S. PATENT DOCUMENTS 8,652,779 B2 2/2014 Turner et al.
8,775,092 B2 7/2014 Colwell et al.
(Continued)

FOREIGN PATENT DOCUMENTS

WO 2016164363 A1 10/2016

OTHER PUBLICATIONS

F. Thei, M. Bennati, M. Rossi, M. Crescentini and M. Tartagni, "Concurrent Acquisition Approach for High Resolution Sensor Arrays," 2010 First International Conference on Sensor Device Technologies and Applications, 2010, pp. 94-99.*
(Continued)

*Primary Examiner* — Jesse P Frumkin

(57) ABSTRACT

A method for processing sequencing data, including: (i) generating, by a sequencing platform, a plurality of sequencing signals from a sequencing operation, each of the plurality of sequencing signals representing a genetic sequence; (ii) sampling, by a controller, each of the plurality of sequencing signals at a Nyquist rate of the sequencing platform to generate an upsampled signal; (iii) receiving, for each of the plurality of sequencing signals, the respective upsampled signal and information associated with the respective sequencing signal, comprising a base pair read number and a time stamp for the respective sequencing signal; (iv) packaging, by the controller for each sequencing signal, the received upsampled signal, base pair read number, and time stamp into a data packet; (v) organizing the packaged data packets into a multiplexed single data stream; and (vi) transmitting the multiplexed single data stream to a remote system.

15 Claims, 3 Drawing Sheets

(51) Int. Cl.
*G16B 50/10* (2019.01)
*G16B 50/50* (2019.01)
*C12Q 1/6869* (2018.01)
*H04L 67/12* (2022.01)
*H04L 47/34* (2022.01)

(52) U.S. Cl.
CPC ............ *H04L 47/34* (2013.01); *C12Q 1/6869* (2013.01); *H04L 67/12* (2013.01)

(56) References Cited

U.S. PATENT DOCUMENTS

| | | |
|---|---|---|
| 9,528,152 B2 | 12/2016 | Sun et al. |
| 2008/0182757 A1 | 7/2008 | Heiner et al. |
| 2011/0158133 A1* | 6/2011 | Boland ................ H04Q 3/0045 370/260 |
| 2014/0248608 A1 | 9/2014 | Barrall et al. |
| 2015/0134267 A1* | 5/2015 | Patterson ............... G16B 30/00 702/19 |
| 2016/0328358 A1* | 11/2016 | Helgesen ............. C12Q 1/6869 |
| 2017/0091381 A1* | 3/2017 | Fernandez-Gomez ...................... G16B 30/00 |
| 2017/0168040 A1* | 6/2017 | Turner ................... B82Y 15/00 |
| 2020/0110752 A1* | 4/2020 | Smith ............... G06F 16/24568 |

OTHER PUBLICATIONS

Wikipedia, "Multiplexing," (https://en.wikipedia.org/wiki/Multiplexing), 8 pages, downloaded Feb. 4, 2022.*
Wikipedia, "Nyquist frequency," (https://en.wikipedia.org/wiki/Nyquist_frequency), 2 pages, downloaded Feb. 4, 2022.*
Wikipedia, "Nyquist rate," (https://en.wikipedia.org/wiki/Nyquist_rate), 3 pages, downloaded Feb. 4, 2022.*
Wikipedia, "Upsampling," (https://en.wikipedia.org/wiki/Upsampling), 3 pages, downloaded Feb. 4, 2022.*

* cited by examiner

COMPRESSION AND ANNOTATION OF DIGITAL WAVEFORMS FROM SERIAL READ NEXT GENERATION SEQUENCING TO SUPPORT REMOTE COMPUTING BASE CALLING

CROSS-REFERENCE TO RELATED APPLICATION

This application claims priority to U.S. Patent Application Ser. No. 62/490,720, filed Apr. 27, 2017, and entitled "Compression and Annotation of Digital Waveforms from Serial Read Next Generation Sequencing to Support Remote Computing Base Calling," the entire disclosure of which is incorporated herein by reference.

FIELD OF THE DISCLOSURE

The present disclosure is directed generally to methods and systems for real-time annotation of next-generation nucleic acid sequencing.

BACKGROUND

Next-generation sequencing (NGS) is an important tool for genomics research, and has numerous applications for discovery, diagnosis, and other methodologies. Although NGS innovations continue to increase the speed of nucleic acid sequencing, it remains a costly and lengthy process. The amount of time required to sequence samples can significantly impact clinical decision-making, thereby reducing the clinical utility of sequencing, since complex therapy decisions must be made quickly.

For example, traditional microbiological laboratory procedures typically result in a definitive pathogen identification and antibiotic susceptibility, if the pathogen is bacterial, within several days after sample acquisition from the patient. In many cases the therapy decision initiated by the care team, made before definitive identification, is not optimally matched to the clinical susceptibility of the pathogen. On the other hand, ineffective therapy resulting from therapy initiated before definitive identification can result in further compromise or death of the patient.

Real-time or near real-time analysis of nucleic acid samples using next-generation sequencing techniques is an attractive and promising approach that could produce actionable results within a significantly shorter timeframe. However, sequencing speed is a major limiting factor to this approach. Raw sequencing signals are typically generated by a sequencing platform and used to generate a plurality of sub files (representing regions, chromosomes, and other organizational levels). Once the raw sub files are complete, the sequencer converts the information into a complete representation of the genome which was just completed. This process is slow and requires a significant amount of sequencing information before interpretation and analysis of the sample can be performed. Indeed, current NGS solutions that attempt to provide rapid and accurate sequencing for sample identification, these solutions are not optimal.

SUMMARY OF THE DISCLOSURE

There is a continued need for real-time or near real-time processing and analysis of next-generation sequencing data. The present disclosure is directed to inventive methods and systems for real-time or near real-time analysis of next-generation nucleic acid sequencing information. Various embodiments and implementations herein are directed to a system that receives a sequencing signal from a sequencing operation for a sample. The system sequences nucleic acid molecules to generate a plurality of sequencing signals, and samples each of the plurality of sequencing signals at a Nyquist rate of the sequencing platform to generate a sampling signal. Each of the received sampling signals is packaged into a data packet together with a base pair read number and a time stamp for the respective sequencing signal from which the sampling signal was generated. The data packets are multiplexed into a single data stream and transmitted to a remote system.

Generally in one aspect, is a method for processing sequencing data. The method includes: (i) generating, by a sequencing platform, a plurality of sequencing signals from a sequencing operation for a sample, each of the plurality of sequencing signals representing a genetic sequence; (ii) sampling, by a controller, each of the plurality of sequencing signals at a Nyquist rate of the sequencing platform to generate an upsampled signal; (iii) receiving, for each of the plurality of sequencing signals, the respective upsampled signal and information associated with the respective sequencing signal, comprising a base pair read number and a time stamp for the respective sequencing signal; (iv) packaging, by the controller for each sequencing signal, the received upsampled signal, base pair read number, and time stamp into a data packet; (v) organizing the packaged data packets into a multiplexed single data stream; and (vi) transmitting the multiplexed single data stream to a remote system.

According to an embodiment, the plurality of data packets are generated and transmitted to the remote system in real-time during the sequencing operation.

According to an embodiment, the method further includes analyzing, at the remote system, the received sequencing signals.

According to an embodiment, the method further includes annotating, at the remote system, a received sequencing signal. According to an embodiment, the annotation comprises information about: (i) whether the sequencing signal comprises a nucleic acid; (ii) a direction of a sequencing read; and/or (iii) a speed of a sequencing read.

According to an embodiment, the method further includes identifying, by the remote system, a problematic sequencing signal.

According to an embodiment, the method further includes transmitting, by the remote system, a command to the sequencing platform.

According to an embodiment, the method further includes receiving, from the remote system, a command for the sequencing platform.

According to an embodiment, the command comprises an instruction to: (i) re-read all or a portion of a nucleic acid molecule being sequenced; (ii) eject a nucleic acid molecule being sequenced; (iii) redirect a nucleic acid molecule being sequenced; and/or (iv) change a sequencing speed of a nucleic acid molecule being sequenced.

According to an embodiment, the method further includes implementing, by the sequencing platform, the received command.

According to an aspect is a system for processing sequencing data. The system includes: (i) a sequencing information system configured to: generate, by a sequencing platform, a plurality of sequencing signals from a sequencing operation for a sample, each of the plurality of sequencing signals representing a genetic sequence; sample each of the plurality of sequencing signals to generate an upsampled signal; receive, for each of the plurality of sequencing signals, the respective upsampled signal and information associated with the respective sequencing signal, comprising a base pair read number and a time stamp for the respective sequencing signal; package the received upsampled signal, base pair read number, and time stamp into a data packet for each sequencing signal; and transmit the packaged data packets via a communication interface; and (ii) a remote system configured to: analyze sequencing signals received via the transmitted data stream; and transmit, to the sequencing information system via a communication interface, a command for the sequencing platform; wherein the sequencing information system is further configured to implement the received command.

According to an embodiment, the remote system is further configured to annotate a received sequencing signal. According to an embodiment, the annotation comprises information about: (i) whether the sequencing signal comprises a nucleic acid; (ii) a direction of a sequencing read; and/or (iii) a speed of a sequencing read.

According to an embodiment, the sequencing information system is configured to generate and transmit the plurality of data packets to the remote system in real-time during the sequencing operation.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method for real-time or near real-time analysis of next-generation nucleic acid sequencing information. More generally, Applicant has recognized and appreciated that it would be beneficial to provide a system that enables rapid and efficient analysis of sequencing signals. The system, which may optionally comprise a sequencing platform, generates or receives a plurality of sequencing signals each representing a nucleic acid molecule in a signal. Each of the sequencing signals is sampled at the Nyquist rate of the sequencing platform to generate a sampling signal. Each sampling signal is packaged into a data packet together with a base pair read number and a time stamp for the respective sequencing signal from which the sampling signal was generated. The data packets are multiplexed into a single data stream and transmitted to a remote system. According to an embodiment, the remote system unpackages and analyzes the received data packets, and can optionally send commands back to the system and/or the sequencing platform based at least in part on the content of the unpackaged sampling signal.

Figure 1:
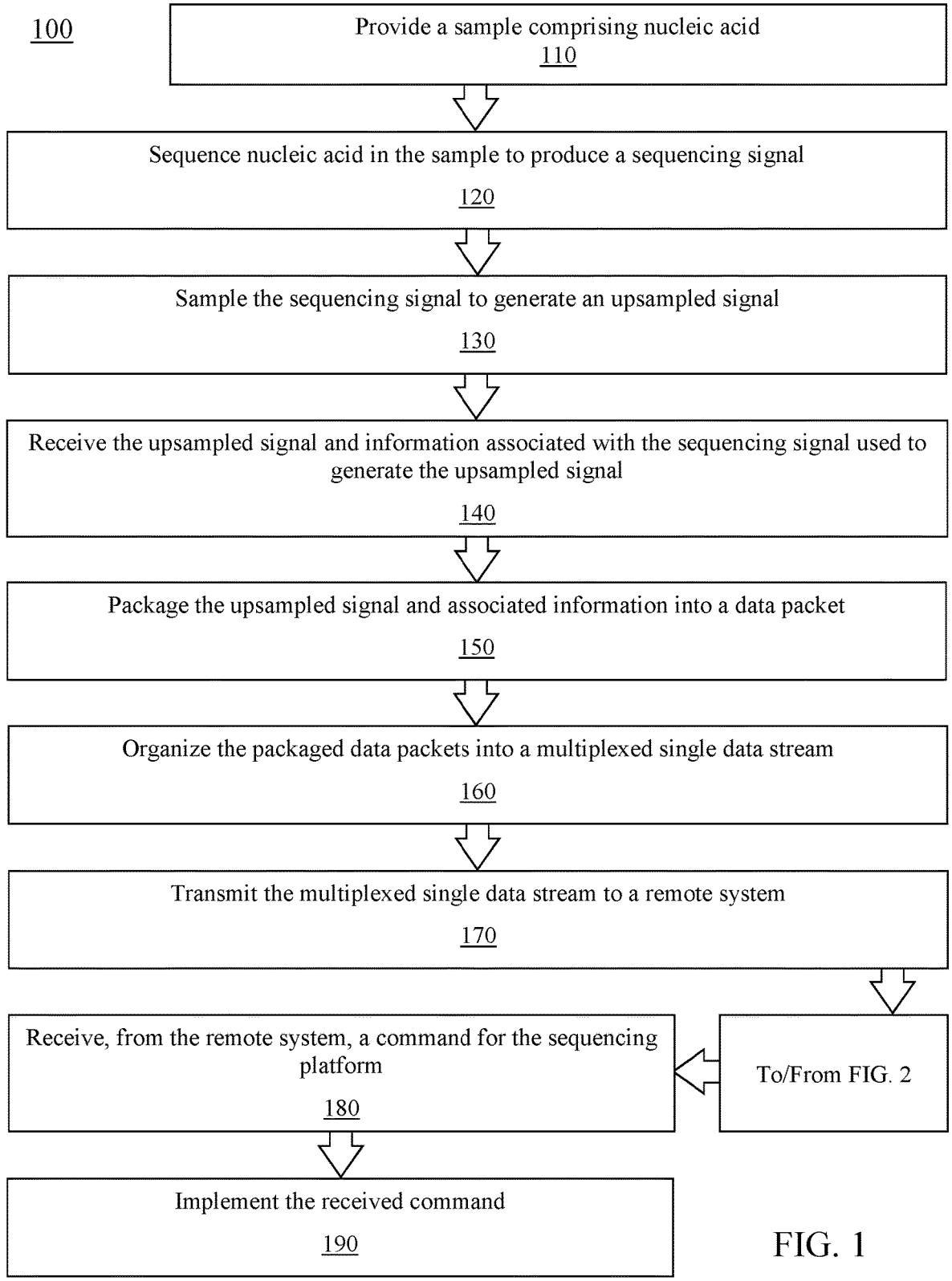
FIG. 1 is a flowchart of a method for processing sequencing information, in accordance with an embodiment.

Referring to FIG. 1, in one embodiment, is a flowchart of a method 100 for packaging and transmitting sequencing information using a sequencing information system. The sequencing information system may be any of the systems described or otherwise envisioned herein, and may comprise any of the components or modules described or otherwise envisioned herein.

At step 110 of the method, a sample comprising or potentially comprising nucleic acid to be sequenced is provided or received. The sample may comprise nucleic acid from one or more microorganisms such as bacteria, viruses, fungi, and/or from plants or animals, among many other sources. A sample may comprise nucleic acid molecules from one organism or from multiple organisms. Samples may be obtained in a clinical setting, from the environment, from indoor or outdoor surfaces, or from any other source. It is recognized that there is no limitation to the source of the sample, or the nucleic acid(s) in the sample. The sample and/or the nucleic acids therein may be prepared for sequencing using any method for preparation, which may be at least in part dependent upon the sequencing platform. According to an embodiment, the nucleic acids may be extracted, purified, and/or amplified, among many other preparations or treatments. For some platforms, the nucleic acid may be fragmented using any method for nucleic acid fragmentation, such as shearing, sonication, enzymatic fragmentation, and/or chemical fragmentation, among other methods, and may be ligated to a sequencing adaptor or any other molecule or ligation partner.

At step 120 of the method, during a sequencing operation a sequencing platform sequences a plurality of nucleic acid molecules in the sample, thereby generating a plurality of sequencing signals in real time. Each sequencing signal represents a genetic sequence obtained from one of the plurality of nucleic acid molecules in the sample. The sequencing signal is any signal such as a waveform that represents the sequence of the nucleic acid being sequenced, and can be any signal representative of a genetic sequence.

The sequencing platform can be any sequencing platform, including but not limited to any systems described or otherwise envisioned herein. For example, the sequencing platform can be a real-time single-molecule sequencing platform, such as a pore-based sequencing platform, although many other sequencing platforms are possible.

According to an embodiment, the sequencing platform is a pore-based sequencing platform. As a single nucleic acid strand passes through the pore, the bases affect a current flow through the pore as detected by a current meter. Each type of base (A, C, G, and T) has a slightly different effect on the current flow through the pore, and thus the waveform generated by the changing current flow is representative of the sequence of nucleic acid bases that pass through the pore. In many systems the generated waveform is interpreted to reveal the underlying genetic sequence of the nucleic acid strand that passed through the pore.

According to an embodiment, the sequencing signal is communicated to or from the sequencing platform to a controller or other analysis module for processing or analysis. For example, according to one embodiment the sequencing platform may comprise a controller or other analysis module for processing or analysis. According to another embodiment, the sequencing platform communicates the generated sequencing signal, in real-time or at certain time points, to a local or remote controller or other analysis module for processing or analysis.

At step 130 of the method, a controller or signal processor of the sequencing information system samples one or more of the plurality of sequencing signals to generate an upsampled signal. The controller or signal processor can sample a sequencing signal at a rate set by a user, a rate set by the system, or any other rate. According to an embodiment, the controller or signal processor samples a sequencing signal at the Nyquist rate, which is the minimum rate at which the sequencing signal can be sampled without introducing errors. The Nyquist rate is twice the highest frequency in the signal to be recovered. The Nyquist rate may be at least in part dependent upon one or more parameters of the generated sequencing signal and thus the controller or signal processor may analyze a portion of the sequencing signal to determine the appropriate Nyquist rate for the signal. For example, the rate of the strand migrating through the pore and generating a waveform or other signal is variable. Pursuant to an embodiment in which the signal is sampled at the Nyquist rate, the controller or signal processor samples the signal at a rate at twice the rate of the variable pore traverse, although other sampling rates are possible.

It should be noted that the process of upsampling can optionally include the step of interpolation. According to an embodiment, the upsampled signal is communicated to or from the controller or signal processor to another analysis module or device for processing or analysis. For example, the controller or signal processor may communicate the generated upsampled signal to a local or remote analysis module or device for processing or analysis.

At step 140 of the method the system receives, for each of the plurality of sequencing signals, the respective upsampled signal and information associated with the respective sequencing signal. For example, the controller or any other component or module of the sequencing information system can receive one of more upsampled signals as well as the information associated with that upsampled signal and/or with the sequencing signal used to generate the upsampled signal.

According to an embodiment, the information associated with the respective sequencing signal can comprise one or many data points. For example, the information may include a base pair read number for the read, which is a sequential number of the base pair for a strand being sequenced. The information may also comprise a time stamp for the respective sequencing signal, which can be a precise time stamp for a particular base pair or k-mer. The time stamp information may, for example, facilitate downstream asynchronous reconstruction.

According to an embodiment, the sequencing signals are generated from a sequencing matrix or other multiplexed sequencing platform in which multiple sequences are generated simultaneously. Thus, the information associated with the respective sequencing signal can comprise location information identifying where within the sequencing platform the sequence was obtained. For example, with reference to a pore-based sequencing platform, the location information may comprise an address of, or other location information for, the pore from which the sequencing signal is being or has been generated.

According to an embodiment, the information associated with the respective sequencing signal can comprise information or annotations provided by the sequencing platform. For example, the sequencing platform may provide information about the device and/or about the sequencing operation or process, including but not limited to information about the nucleic acid/enzyme complex attachment, an open pore, a blocked pore, a hairpin, a barcode, and/or any other information about the device and/or about the sequencing operation or process.

According to an embodiment, the information associated with the respective sequencing signal can comprise any metadata that may be beneficial, selected, programmed, or otherwise provided or requested. For example, the metadata may comprise information about a read, the sample, the sequencing platform, the date, the location of the sequencing platform, parameters of the sequencing platform, and/or any other provided or requested metadata information.

At step 150 of the method, the controller or any other component or module of the sequencing information system packages the received upsampled signal and associated information into a data packet. As described herein, the information associated with the upsampled signal can be any of a wide variety of different types of information. The header of the data packet may comprise, for example, any of the information associated with the upsampled signal. The sequencing information system can compress or otherwise process the data as it is packaged into the data packets, and it should be understood that there are a wide variety of methods and systems for packaging data.

At step 160 of the method, which may be performed together with step 150 or after step 150, the plurality of data packets are organized, packaged, arranged, or otherwise formatted into a multiplexed single data stream. This facilitates and accelerates downstream transmission of the data. The plurality of data packets can be organized into a multiplexed single data stream using any method or system for data processing or packaging.

At step 170 of the method, which may be performed together with steps 150 and/or 160 or after steps 150 and/or 160 of the method, the sequencing information system transmits the multiplexed single data stream to a remote system. The multiplexed single data stream can be transmitted using any method or system for communication. For example, the multiplexed single data stream can be transmitted via any wired and/or wireless communication system or network. According to an embodiment, the data packets are generated and transmitted to the remote system in real-time during the sequencing operation.

The remote system can be any remote computer system configured to receive the data packets. The remote system may analyze the received information, may store the received information, and/or may communicate the received information to another system. According to an embodiment, the remote system is located remote from the sequencing information system, where remote may refer to a physical separation or physical distance between the sequencing information system and the remote system. For example, the remote system may be physical distinct from the sequencing information system but may be located in the same room, building, facility, or approximate physical location. Alternatively, the remote system may be located in a different physical location such as a different building, region, state, country, or other location. The remote system can be any computer system, including a server, bank of servers, cloud-based service, or any other computer system.

Figure 2:
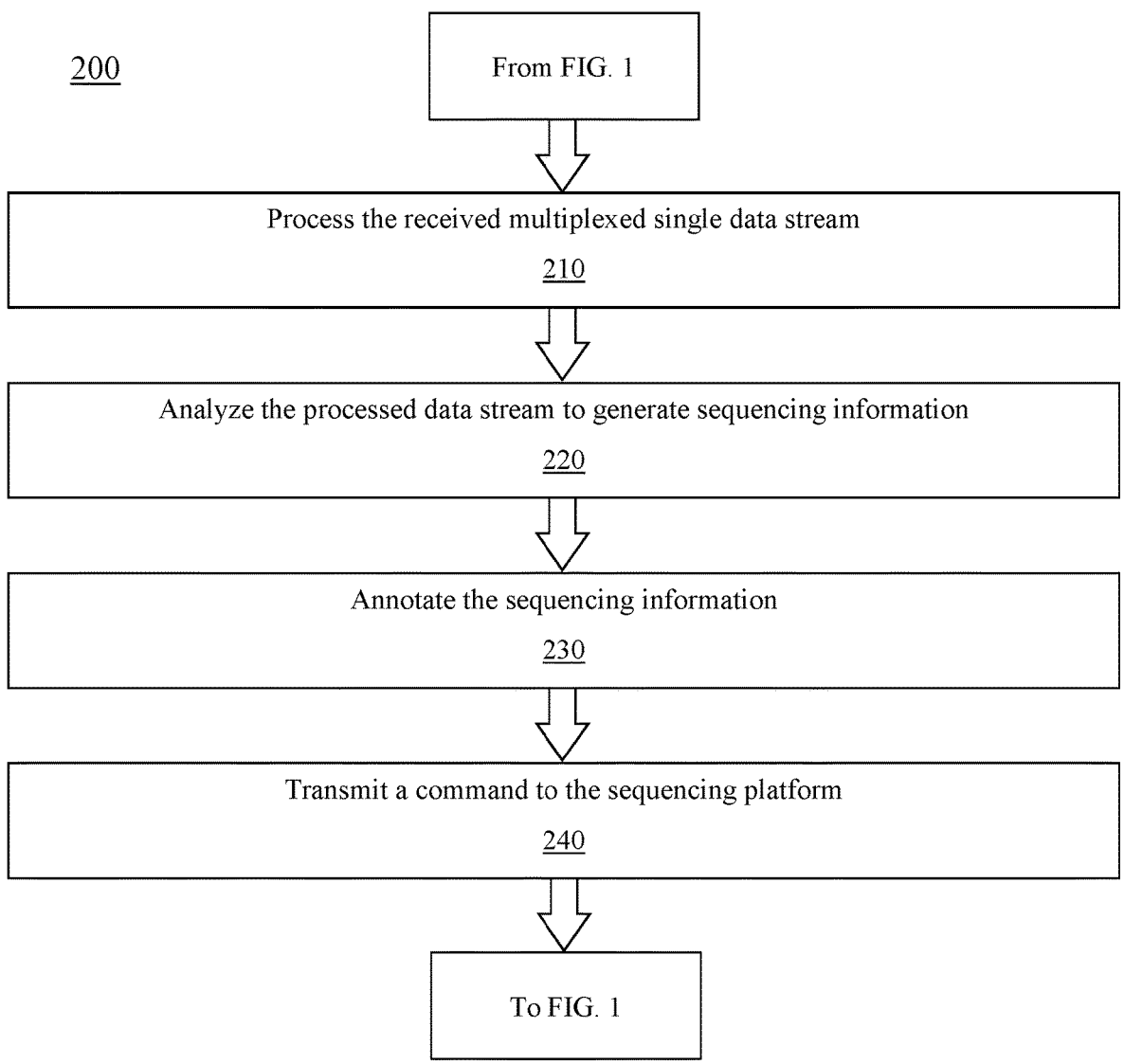
FIG. 2 is a flowchart of a method for processing sequencing information, in accordance with an embodiment.

Referring to FIG. 2, in one embodiment, is a flowchart of a method 200 for analyzing, by a remote system, received sequencing information. The remote system may be any of the systems described or otherwise envisioned herein, and may comprise any of the components or modules described or otherwise envisioned herein.

At step 210 of the method, a controller or other signal processing component of the remote system receives and processes the multiplexed single data stream transmitted by the sequencing information system. For example, the controller or other signal processing component of the remote system may de-multiplex, downsample, or otherwise process the received multiplexed single data stream. The remote system may save the processed information in memory and/or may proceed to real-time analysis of the processed information. Due in part to the relatively small bandwidth of the data packets and efficient transmission methods and systems, the received information can be de-multiplexed, downsampled, and/or otherwise decoded or processed to generate specific sequencing signals or streams with minimal error or data loss.

At step 220 of the method, a controller or other signal processing component of the remote system analyzes the received information. This analysis may be any analysis configured or designed to accomplish one or more goals or directives of the sequencing operation. According to an embodiment, a sequencing signal can be analyzed to determine a sequence of the nucleic acid molecule from which the sequencing signal was generated. For example, the sequencing signal and the base pair read number can be used to reconstruct the sequencing waveform.

According to an embodiment, after a sequence of the nucleic acid molecule is determined, storage and communication to other processes can be optimized and accelerated by remodeling the time domain waveforms as quaternary 2-bit codes. Four-level pulse amplitude modulation (PAM-4) schemes exist, and many do not require DC balancing. Applying this to pore-based sequencing, for example, real-time reads that require conversion of base-called waveforms to reflected binary code or Gray code representing each base as a specific voltage and a 2-bit number, further accelerate analog and digital computations. In addition, other metadata can be aligned and preserved in this new binary format.

According to an embodiment, the remote system can account for transmission or other processing errors. For example, the sequencing signal and the base pair read number can be used to reconstruct the sequencing waveform, and imperfect remote computing transmission channel characteristics may occur. Sample retries and re-transmit requests may provide challenges in the remote system, however the input buffers to the system can recover when data is received out of order or when packets are delayed in route.

At step 230 of the method, the remote system annotates a received and/or processed sequencing signal. This annotation may be based at least in part on the information associated with the original sequencing signal, packaged into a data packet, and transmitted to the remote system. This may include the read number, time stamp, and/or any other information. The annotation may be associated with the sequencing signal in memory or via any other method of association.

The annotation may comprise, for example, information about whether the sequencing signal comprises a nucleic acid, a direction of a sequencing read, a speed of a sequencing read, and/or any other information. According to an embodiment, the annotation may comprise an indication that the sequencing signal is problematic, where the problem can be anything that may interfere with determination of a sequence, or accuracy of that determination. For example, the annotation may indicate that a waveform segment does not lend itself to standard base calling. The annotation may also indicate that the waveform segment is problematic, and mark the segment for removal or otherwise prevent it from being utilized in downstream analyses or by another system or process.

At step 240 of the method, the remote system generates and transmits a command to the sequencing information system. The command may be sent via any wired and/or wireless communication network, including but not limited to the communication network utilized in previous steps of the method. The command may be sent to the sequencing information system for processing and implementation, or may be transmitted directly to the sequencing platform for implementation.

The command is based at least in part on the analysis and/or annotation of the sequencing information received by the remote system. For example, as described or otherwise envisioned herein, the remote system analyzes the sequencing information and can identify issues with that information, including but not limited quality issues, interpretation issues, and many other types of issues.

According to an embodiment, the command from the remote system may comprise, for example, an instruction to re-read all or a portion of a nucleic acid molecule being sequenced, an instruction to eject a nucleic acid molecule being sequenced, an instruction to redirect a nucleic acid molecule being sequenced, and/or an instruction to change a sequencing speed of a nucleic acid molecule being sequenced. Many other commands are possible. For example, with a real-time data feed pursuant to the methods and systems described herein, new sequencing approaches may including notifying the sequencer to re-read a particular region of the current strand due to high errors, to verify regions of homo-polymer, and/or to verify specific genes where knowledge relevant to the patient is critical for therapeutic decision, among other approaches. These commands may be to re-read between specific base pairs, eject the strand (if not a target for analysis), or slow the strand to make better reads at critical points of the strand read. These approaches may require, for example, may assume real-time control of the sequencing operation, and may necessitate only a minimal wait time for ejecting the strand from the DNA enzyme complex attachment, and/or ejecting the DNA enzyme complex attachment itself.

At step 180 of the method, the sequencing information system receives the command from the remote system. The command may be sent via any wired and/or wireless communication network, including but not limited to the communication network utilized in previous steps of the method. The command may be received by the sequencing information system for processing and implementation, or may be directly received by the sequencing platform for implementation.

At step 190 of the method, the sequencing information system implements the command. The controller or other element of the sequencing information system may direct the sequencing platform to implement the command, or the sequencing platform may implement the command directly.

According to an embodiment, the method enables the system to extract read information in real-time, provide appropriate annotations, compress the data, and transport it to a real-time processing system. Accordingly, the approach need not wait for sub-files to be assembled, nor does it need to wait for a final file representing the genome to be completed prior to deriving knowledge from the sample. Thus, the approach can send real-time information back to the sequencing platform to improve turn-around time ("TAT" and time to ultimate decisions, among many other improvements.

Figure 3:
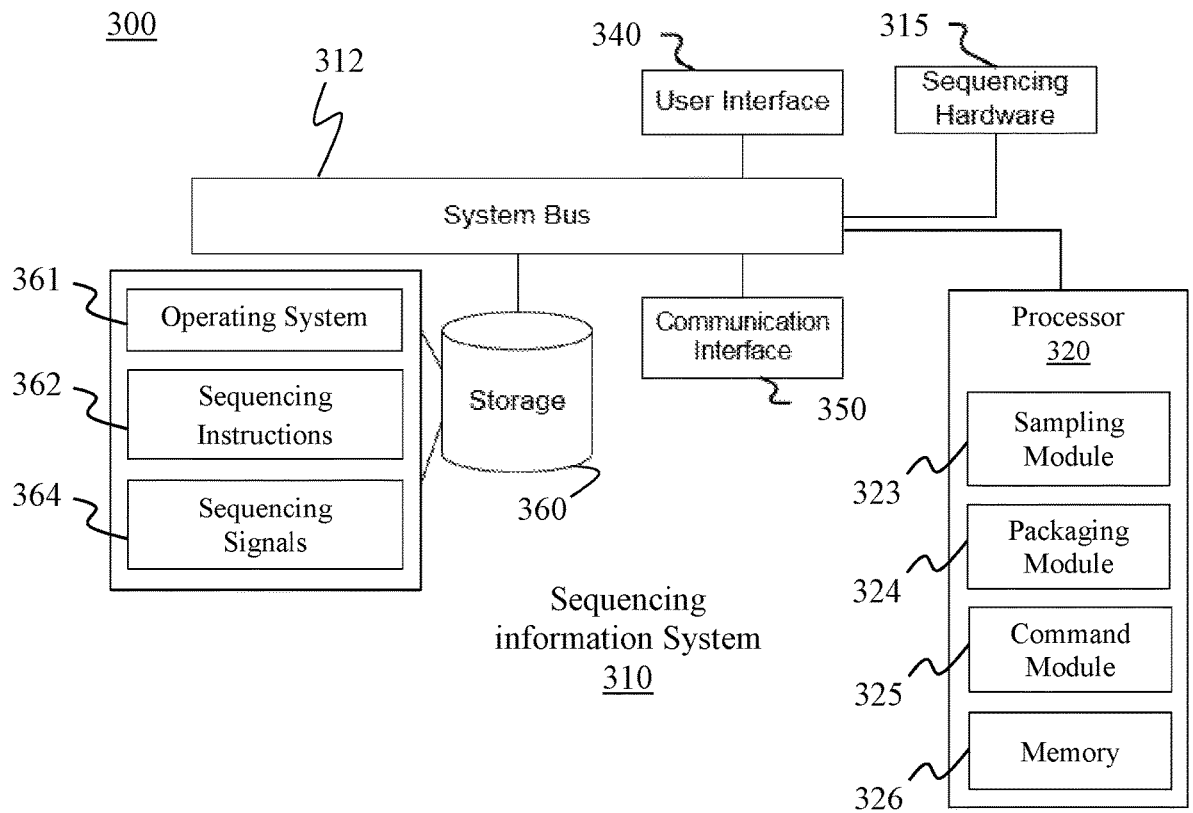
FIG. 3 is a schematic representation of a system for processing sequencing information, in accordance with an embodiment.
Figure 3:
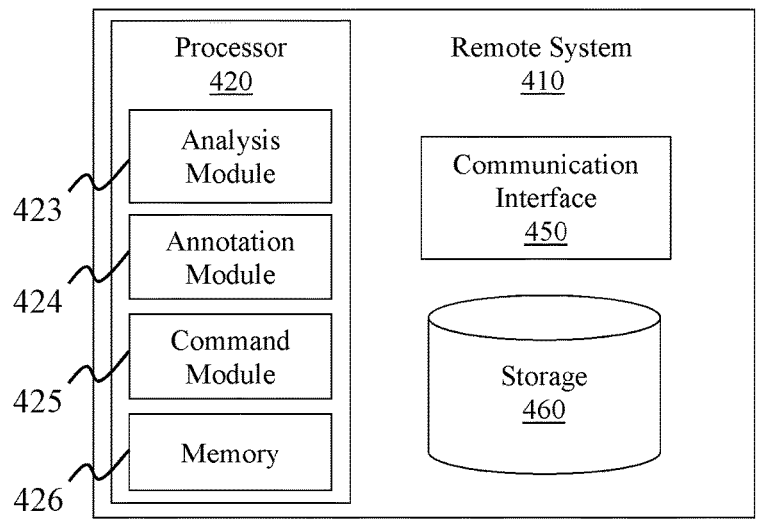

Referring to FIG. 3, in one embodiment, is a schematic representation of a system 300 for analyzing sequencing information using a sequencing information system 310 and a remote system 410. System 300 may be any of the systems described or otherwise envisioned herein, and may comprise any of the components or modules described or otherwise envisioned herein.

According to an embodiment, system 300 comprises a sequencing information system 310, the sequencing information system comprising one or more of a controller 320, memory 326, user interface 340, communications interface 350, and storage 360, interconnected via one or more system buses 312. In some embodiments, such as those where the system comprises or directly implements a sequencer or sequencing platform, the hardware may include additional sequencing platform 315 such as a real-time single-molecule sequencer, including but not limited to a pore-based sequencer, although many other sequencing platforms are possible. It will be understood that FIG. 3 constitutes, in some respects, an abstraction and that the actual organization of the components of the system 300 may be different and more complex than illustrated.

According to an embodiment, sequencing information system 310 comprises a controller 320 capable of executing instructions stored in memory 326 or storage 360 or otherwise processing data. Controller 320 performs one or more steps of the method, and may comprise one or more of the modules described or otherwise envisioned herein. Controller 320 may be formed of one or multiple modules, and can comprise, for example, a memory 326. Controller 320 may take any suitable form, including but not limited to a microprocessor, microcontroller, multiple microcontrollers, circuitry, field programmable gate array (FPGA), application-specific integrated circuit (ASIC), a single processor, or plural processors.

Memory 326 can take any suitable form, including a non-volatile memory and/or RAM. The memory 326 may include various memories such as, for example L1, L2, or L3 cache or system memory. As such, the memory 326 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 300. It will be apparent that, in embodiments where the processor implements one or more of the functions described herein in hardware, the software described as corresponding to such functionality in other embodiments may be omitted.

User interface 340 may include one or more devices for enabling communication with a user such as an administrator. The user interface can be any device or system that allows information to be conveyed and/or received, and may include a display, a mouse, and/or a keyboard for receiving user commands. In some embodiments, user interface 340 may include a command line interface or graphical user interface that may be presented to a remote terminal via communication interface 350. The user interface may be located with one or more other components of the system, or may located remote from the system and in communication via a wired and/or wireless communications network.

Communication interface 350 may include one or more devices for enabling communication with other hardware devices, including but not limited to remote system 410. For example, communication interface 350 may include a network interface card (NIC) configured to communicate according to the Ethernet protocol. Additionally, communication interface 350 may implement a TCP/IP stack for communication according to the TCP/IP protocols. Various alternative or additional hardware or configurations for communication interface 350 will be apparent.

Storage 360 may include one or more machine-readable storage media such as read-only memory (ROM), random-access memory (RAM), magnetic disk storage media, optical storage media, flash-memory devices, or similar storage media. In various embodiments, storage 360 may store instructions for execution by controller 320 or data upon which controller 320 may operate. For example, storage 360 may store an operating system 361 for controlling various operations of sequencing information system 310. Where sequencing information system 310 implements a sequencer and includes sequencing platform 315, storage 360 may include sequencing instructions 362 for operating the sequencing platform 315. Storage 360 may also comprise one or more sequencing signals 364 received from a sequencing platform.

According to an embodiment, system 300 comprises remote system 410 comprising one or more of a controller 420, memory 426, communications interface 450, and storage 460. It will be understood that the schematic representation of remote system 410 in FIG. 3 constitutes, in some respects, an abstraction and that the actual organization of the components of the remote system 410 may be different and more complex than illustrated.

According to an embodiment, remote system 410 comprises a controller 420 capable of executing instructions stored in memory 426 or storage 460 or otherwise processing data. Controller 420 performs one or more steps of the method, and may comprise one or more of the modules described or otherwise envisioned herein. Controller 420 may be formed of one or multiple modules, and can comprise, for example, a memory 426. Controller 420 may take any suitable form, including but not limited to a microprocessor, microcontroller, multiple microcontrollers, circuitry, field programmable gate array (FPGA), application-specific integrated circuit (ASIC), a single processor, or plural processors.

Memory 426 can take any suitable form, including a non-volatile memory and/or RAM. The memory 426 may include various memories such as, for example L1, L2, or L3 cache or system memory. As such, the memory 426 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of remote system 410. It will be apparent that, in embodiments where the processor implements one or more of the functions described herein in hardware, the software described as corresponding to such functionality in other embodiments may be omitted.

Communication interface 450 may include one or more devices for enabling communication with other hardware devices, including but not limited to sequencing information system 310. For example, communication interface 450 may include a network interface card (NIC) configured to communicate according to the Ethernet protocol. Additionally, communication interface 450 may implement a TCP/IP stack for communication according to the TCP/IP protocols. Various alternative or additional hardware or configurations for communication interface 450 will be apparent.

Storage 460 may include one or more machine-readable storage media such as read-only memory (ROM), random-access memory (RAM), magnetic disk storage media, optical storage media, flash-memory devices, or similar storage media. In various embodiments, storage 460 may store instructions for execution by controller 420 or data upon which controller 420 may operate. For example, storage 460 may store an operating system 461 for controlling various operations of remote system 410.

It will be apparent that various information described as stored in storage 360 or 460 may be additionally or alternatively stored in memory 326 or 426. In this respect, memory 326 may also be considered to constitute a storage device and storage 360 or 460 may be considered a memory. Various other arrangements will be apparent. Further, memory 326 or 426 and storage 360 or 460 may both be considered to be non-transitory machine-readable media. As used herein, the term non-transitory will be understood to exclude transitory signals but to include all forms of storage, including both volatile and non-volatile memories.

While sequencing information system 310 and remote system 410 is shown as including one of each described component, the various components may be duplicated in various embodiments. For example, controller 320 or 420 may include multiple microprocessors that are configured to independently execute the methods described herein or are configured to perform steps or subroutines of the methods described herein such that the multiple processors cooperate to achieve the functionality described herein. Further, where one or more components of system 300 is implemented in a cloud computing system, the various hardware components may belong to separate physical systems. For example, controller 320 or 420 may include a first processor in a first server and a second processor in a second server. Many other variations and configurations are possible.

According to an embodiment, controller 320 of sequencing information system 310 comprises one or more modules to carry out one or more functions or steps of the methods described or otherwise envisioned herein. For example, controller 320 may comprise a sampling module 323, a packaging module 324, and/or a command module 325.

According to an embodiment, the sampling module 323 samples one or more of the plurality of sequencing signals 364 to generate an upsampled signal. Sampling module 323 can sample a sequencing signal at a rate set by a user, a rate set by the system, or any other rate. The sampling rate may be at least in part dependent upon one or more parameters of the generated sequencing signal and thus the sampling module 323 may analyze a portion of the sequencing signal to determine the appropriate sampling rate for the signal. It should be noted that the process of upsampling can optionally include the step of interpolation by the sampling module. According to an embodiment, the upsampled signal is communicated to or from the sampling module 323 to another analysis module or device for processing or analysis. For example, the sampling module 323 may communicate the generated upsampled signal to a local or remote analysis module or device for processing or analysis.

According to an embodiment, the packaging module 324 packages the received upsampled signal and associated information into a data packet. As described herein, the information associated with the upsampled signal can be any of a wide variety of different types of information. The packaging module 324 can compress or otherwise process the data as it is packaged into the data packets, and it should be understood that there are a wide variety of methods and systems for packaging data. The packaging module 324 may also organize, package, arrange, or otherwise format the plurality of data packets into a multiplexed single data stream using any method or system for data processing or packaging. The packaging module 324 may then direct the communication interface 350 to transmit the multiplexed single data stream to remote system 410. According to an embodiment, the data packets are generated by packaging module 324 and transmitted to the remote system in real-time during the sequencing operation.

According to an embodiment, the command module 325 receives a command from remote system 410 and implements the command, or directs or triggers implementation of the command by another component of system 310. The command may be received by communication interface 350 and provided to command module 325 where it can be analyzed for implementation. The command may be sent via any wired and/or wireless communication network, including but not limited to the communication network utilized in previous steps of the method.

According to an embodiment, controller 420 of remote system 410 comprises one or more modules to carry out one or more functions or steps of the methods described or otherwise envisioned herein. For example, controller 420 may comprise an analysis module 423, an annotation module 424, and/or a command module 425.

According to an embodiment, the analysis module 423 receives a multiplexed single data stream transmitted by the sequencing information system 310. Analysis module 423 may de-multiplex, downsample, or otherwise process the received multiplexed single data stream. The module may also analyze the received information to accomplish one or more goals or directives of the sequencing operation. According to an embodiment, a sequencing signal can be analyzed by analysis module 423 to determine a sequence of the nucleic acid molecule from which the sequencing signal was generated. For example, the sequencing signal and the base pair read number can be used to reconstruct the sequencing waveform.

According to an embodiment, the annotation module 424 annotates a received and/or processed sequencing signal. This annotation may be based at least in part on the information associated with the original sequencing signal, packaged into a data packet, and transmitted to the remote system. This may include the read number, time stamp, and/or any other information. The annotation may be associated with the sequencing signal in memory or via any other method of association. The annotation may comprise, for example, information about whether the sequencing signal comprises a nucleic acid, a direction of a sequencing read, a speed of a sequencing read, and/or any other information. According to an embodiment, the annotation may comprise an indication that the sequencing signal is problematic, where the problem can be anything that may interfere with determination of a sequence, or accuracy of that determination. Many other annotations are possible.

According to an embodiment, the command module 425 generates and directs transmission of a command to the sequencing information system 310 via communications interface 450. The command is based at least in part on the analysis and/or annotation of the sequencing information received by the remote system. According to an embodiment, the command from the remote system may comprise, for example, an instruction to re-read all or a portion of a nucleic acid molecule being sequenced, an instruction to eject a nucleic acid molecule being sequenced, an instruction to redirect a nucleic acid molecule being sequenced, and/or an instruction to change a sequencing speed of a nucleic acid molecule being sequenced. Many other commands are possible.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for processing sequencing data, comprising:
   generating, by a sequencing platform, a plurality of sequencing signals from a sequencing operation for a sample, each of the plurality of sequencing signals representing a genetic sequence;
   sampling, by a controller, each of the plurality of sequencing signals at a Nyquist rate of the sequencing platform to generate an upsampled signal;
   receiving, for each of the plurality of sequencing signals, the respective upsampled signal and information associated with the respective sequencing signal, comprising a base pair read number and a time stamp for the respective sequencing signal;
   packaging, by the controller for each sequencing signal, the received upsampled signal, base pair read number, and time stamp into a data packet;

organizing the packaged data packets into a multiplexed single data stream; and transmitting the multiplexed single data stream to a remote system.

2. The method of claim 1, wherein the multiplexed single data stream is transmitted to the remote system in real-time during the sequencing operation.

3. The method of claim 1, further comprising:

receiving, by the remote system, the transmitted multiplexed single data stream;

analyzing, by the remote system, the sequencing signals in the transmitted multiplexed single data stream.

4. The method of claim 3, further comprising annotating, by the remote system, the sequencing signals in the transmitted multiplexed single data stream.

5. The method of claim 4, wherein the annotation comprises information about: (i) whether the sequencing signal comprises a nucleic acid; (ii) a direction of a sequencing read; and/or (iii) a speed of a sequencing read.

6. The method of claim 3, further comprising identifying, by the remote system, a problematic sequencing signal.

7. The method of claim 1, further comprising transmitting, by the remote system, a command to the sequencing platform.

8. The method of claim 7, wherein the command comprises an instruction to: (i) re-read all or a portion of a nucleic acid molecule being sequenced; (ii) eject a nucleic acid molecule being sequenced; (iii) redirect a nucleic acid molecule being sequenced; and/or (iv) change a sequencing speed of a nucleic acid molecule being sequenced.

9. The method of claim 1, further comprising receiving, from the remote system, a command for the sequencing platform.

10. The method of claim 7, further comprising implementing, by the sequencing platform, the received command.

11. A system for processing sequencing data, comprising:

a sequencing information system configured to: (i) generate, by a sequencing platform, a plurality of sequencing signals from a sequencing operation for a sample, each of the plurality of sequencing signals representing a genetic sequence; (ii) sample each of the plurality of sequencing signals to generate an upsampled signal; (iii) receive, for each of the plurality of sequencing signals, the respective upsampled signal and information associated with the respective sequencing signal, comprising a base pair read number and a time stamp for the respective sequencing signal; (iv) package the received upsampled signal, base pair read number, and time stamp into a data packet for each sequencing signal; and (v) transmit the packaged data packets via a communication interface; and a remote system configured to: (i) analyze sequencing signals received via the transmitted data stream; and (ii) transmit, to the sequencing information system via a communication interface, a command for the sequencing platform;

wherein the sequencing information system is further configured to implement the received command.

12. The system of claim 11, wherein the remote system is further configured to annotate a received sequencing signal.

13. The system of claim 12, wherein the annotation comprises information about: (i) whether the sequencing signal comprises a nucleic acid; (ii) a direction of a sequencing read; and/or (iii) a speed of a sequencing read.

14. The system of claim 11, wherein the command comprises an instruction to: (i) re-read all or a portion of a nucleic acid molecule being sequenced; (ii) eject a nucleic acid molecule being sequenced; (iii) redirect a nucleic acid molecule being sequenced; and/or (iv) change a sequencing speed of a nucleic acid molecule being sequenced.

15. The system of claim 11, wherein the sequencing information system is configured to generate and transmit the data packets to the remote system in real-time during the sequencing operation.

\* \* \* \* \*